United States Patent
Forde

(10) Patent No.: US 10,368,942 B2
(45) Date of Patent: Aug. 6, 2019

(54) DEVICES AND METHODS FOR TREATING CARDIAC TISSUE

(71) Applicant: W.L. Gore & Associates, Inc., Flagstaff, AZ (US)

(72) Inventor: Sean Forde, Watertown, MA (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 15/043,397

(22) Filed: Feb. 12, 2016

(65) Prior Publication Data
US 2016/0157912 A1    Jun. 9, 2016

Related U.S. Application Data

(63) Continuation of application No. 11/516,144, filed on Sep. 6, 2006, now Pat. No. 9,259,267.
(Continued)

(51) Int. Cl.
| | | |
|---|---|---|
| A61B 18/00 | (2006.01) |
| A61B 18/14 | (2006.01) |
| A61B 18/18 | (2006.01) |
| A61B 18/24 | (2006.01) |
| A61B 18/22 | (2006.01) |

(Continued)

(52) U.S. Cl.
CPC .......... *A61B 18/1492* (2013.01); *A61B 18/00* (2013.01); *A61B 18/18* (2013.01); *A61B 18/1815* (2013.01); *A61B 18/24* (2013.01); *A61B 17/12022* (2013.01); *A61B 18/22* (2013.01); *A61B 2017/00575* (2013.01); *A61B 2018/00291* (2013.01); *A61B 2018/00351* (2013.01); *A61B 2018/1861* (2013.01); *A61B 2018/2238* (2013.01); *A61B 2018/2244* (2013.01)

(58) Field of Classification Search
CPC .................. A61B 18/1492; A61B 18/1815
See application file for complete search history.

(56) References Cited

U.S. PATENT DOCUMENTS

| 3,874,388 A | 4/1975 | King et al. |
| 4,007,743 A | 2/1977 | Blake |
(Continued)

FOREIGN PATENT DOCUMENTS

| EP | 0317067 A2 | 5/1989 |
| EP | 0553259 B1 | 3/1995 |
(Continued)

OTHER PUBLICATIONS

"Elastic Deployment" SMST-2000 Proceedings of the International Conference on Shape Memory and Superelastic Technologies, 3 pages (Apr. 30-May 4, 2000).
(Continued)

*Primary Examiner* — Michael J D Abreu

(57) ABSTRACT

The invention generally relates to devices and methods for treating cardiac tissue, including percutaneous closure of cardiac openings such as a patent foramen ovale (PFO) and obliteration of the cardiac cul-de-sacs. The invention includes a device having at least one elongated member. The elongated member has a first material and a second material interwoven with at least a portion of the first material. The second material is capable of transferring energy to tissue in need of treatment.

7 Claims, 13 Drawing Sheets

Related U.S. Application Data

(60) Provisional application No. 60/734,558, filed on Nov. 8, 2005, provisional application No. 60/714,374, filed on Sep. 6, 2005.

(51) Int. Cl.
*A61B 17/12* (2006.01)
*A61B 17/00* (2006.01)

(56) References Cited

U.S. PATENT DOCUMENTS

| | | |
|---|---|---|
| 4,696,300 A | 9/1987 | Anderson |
| 4,710,192 A | 12/1987 | Liotta et al. |
| 4,832,048 A | 5/1989 | Cohen |
| 4,836,204 A | 6/1989 | Landymore et al. |
| 4,902,508 A | 2/1990 | Badylak et al. |
| 4,917,089 A | 4/1990 | Sideris |
| 4,921,484 A | 5/1990 | Hillstead |
| 4,944,741 A | 7/1990 | Hasson |
| 4,945,912 A | 8/1990 | Langberg |
| 4,946,440 A | 8/1990 | Hall |
| 4,956,178 A | 9/1990 | Badylak et al. |
| 4,967,765 A | 11/1990 | Turner et al. |
| 5,003,990 A | 4/1991 | Osypka |
| 5,007,908 A | 4/1991 | Rydell |
| 5,021,059 A | 6/1991 | Kensey et al. |
| 5,025,799 A | 6/1991 | Wilson |
| 5,108,420 A | 4/1992 | Marks |
| 5,156,613 A | 10/1992 | Sawyer |
| 5,171,259 A | 12/1992 | Inoue |
| 5,176,687 A | 1/1993 | Hasson et al. |
| 5,217,435 A | 6/1993 | Kring |
| 5,222,974 A | 6/1993 | Kensey et al. |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,334,217 A | 8/1994 | Das |
| 5,370,644 A | 12/1994 | Langberg |
| 5,385,156 A | 1/1995 | Olivia |
| 5,423,882 A | 6/1995 | Jackman et al. |
| 5,425,744 A | 6/1995 | Fagan et al. |
| 5,433,727 A | 7/1995 | Sideris |
| 5,451,235 A | 9/1995 | Lock et al. |
| 5,484,385 A | 1/1996 | Rishton |
| 5,486,185 A | 1/1996 | Freitas et al. |
| 5,486,193 A | 1/1996 | Freitas et al. |
| 5,507,744 A | 4/1996 | Tay et al. |
| 5,507,811 A | 4/1996 | Koike et al. |
| 5,540,681 A | 7/1996 | Strul et al. |
| 5,573,533 A | 11/1996 | Strul |
| 5,578,045 A | 11/1996 | Das |
| 5,597,378 A | 1/1997 | Jervis |
| 5,620,461 A | 4/1997 | Muijs Van De Moer et al. |
| 5,620,479 A | 4/1997 | Diederich |
| 5,626,599 A | 5/1997 | Bourne et al. |
| 5,630,837 A | 5/1997 | Crowley |
| 5,634,936 A | 6/1997 | Linden et al. |
| 5,636,634 A | 6/1997 | Kordis et al. |
| 5,649,950 A | 6/1997 | Bourne et al. |
| 5,653,684 A | 8/1997 | Laptewicz et al. |
| 5,669,934 A | 9/1997 | Sawyer |
| 5,676,662 A | 10/1997 | Fleischhacker et al. |
| 5,683,411 A | 11/1997 | Kavteladze et al. |
| 5,690,675 A | 11/1997 | Sawyer et al. |
| 5,702,421 A | 12/1997 | Schneidt |
| 5,709,707 A | 1/1998 | Lock et al. |
| 5,725,552 A | 3/1998 | Kotula et al. |
| 5,733,294 A | 3/1998 | Forber et al. |
| 5,733,337 A | 3/1998 | Carr, Jr. et al. |
| 5,741,249 A | 4/1998 | Moss et al. |
| 5,741,297 A | 4/1998 | Simon |
| 5,749,895 A | 5/1998 | Sawyer et al. |
| 5,797,905 A | 8/1998 | Fleischman et al. |
| 5,797,960 A | 8/1998 | Stevens et al. |
| 5,800,428 A | 9/1998 | Nelson et al. |
| 5,800,478 A | 9/1998 | Chen et al. |
| 5,807,384 A | 9/1998 | Mueller |
| 5,810,810 A | 9/1998 | Tay et al. |
| 5,810,884 A | 9/1998 | Kim |
| 5,823,956 A | 10/1998 | Roth et al. |
| 5,846,261 A | 12/1998 | Kotula et al. |
| 5,849,028 A | 12/1998 | Chen |
| 5,853,422 A | 12/1998 | Huebsch et al. |
| 5,861,003 A | 1/1999 | Latson et al. |
| 5,865,791 A | 2/1999 | Whayne et al. |
| 5,879,366 A | 3/1999 | Shaw et al. |
| 5,893,856 A | 4/1999 | Jacob et al. |
| 5,895,412 A | 4/1999 | Tucker |
| 5,904,703 A | 5/1999 | Gilson |
| 5,919,200 A | 7/1999 | Stambaugh et al. |
| 5,927,284 A | 7/1999 | Borst et al. |
| 5,944,738 A | 8/1999 | Amplatz et al. |
| 5,948,011 A | 9/1999 | Knowlton |
| 5,954,719 A | 9/1999 | Chen et al. |
| 5,955,110 A | 9/1999 | Patel et al. |
| 5,957,919 A | 9/1999 | Laufer |
| 5,964,782 A | 10/1999 | Lafontaine et al. |
| 5,971,980 A | 10/1999 | Sherman |
| 5,976,174 A | 11/1999 | Ruiz |
| 5,993,844 A | 11/1999 | Abraham et al. |
| 5,997,575 A | 12/1999 | Whitson et al. |
| 6,004,269 A | 12/1999 | Crowley et al. |
| 6,004,316 A | 12/1999 | Laufer |
| 6,010,517 A | 1/2000 | Baccaro |
| 6,015,378 A | 1/2000 | Borst et al. |
| 6,016,811 A | 1/2000 | Knopp et al. |
| 6,024,756 A | 2/2000 | Huebsch et al. |
| 6,030,379 A * | 2/2000 | Panescu ............ A61B 18/1492 606/34 |
| 6,063,080 A | 5/2000 | Nelson et al. |
| 6,063,085 A | 5/2000 | Tay et al. |
| 6,077,291 A | 6/2000 | Das |
| 6,080,182 A | 6/2000 | Shaw et al. |
| 6,086,581 A | 7/2000 | Reynolds et al. |
| 6,086,610 A | 7/2000 | Duerig et al. |
| 6,102,926 A | 8/2000 | Tartaglia et al. |
| 6,106,520 A | 8/2000 | Laufer et al. |
| 6,106,532 A | 8/2000 | Koike et al. |
| 6,117,159 A | 9/2000 | Huebsch et al. |
| 6,123,718 A | 9/2000 | Tu et al. |
| 6,132,438 A | 10/2000 | Fleischman et al. |
| 6,135,997 A | 10/2000 | Laufer et al. |
| 6,143,037 A | 11/2000 | Goldstein et al. |
| 6,152,144 A | 11/2000 | Lesh et al. |
| 6,152,918 A | 11/2000 | Padilla et al. |
| 6,165,183 A | 12/2000 | Kuehn et al. |
| 6,171,329 B1 | 1/2001 | Shaw et al. |
| 6,174,322 B1 | 1/2001 | Schneidt |
| 6,187,039 B1 | 2/2001 | Hiles et al. |
| 6,200,313 B1 | 3/2001 | Abe et al. |
| 6,206,907 B1 | 3/2001 | Marino et al. |
| 6,212,426 B1 | 4/2001 | Swanson |
| 6,214,029 B1 | 4/2001 | Thill et al. |
| 6,221,092 B1 | 4/2001 | Koike et al. |
| 6,231,516 B1 | 5/2001 | Keilman et al. |
| 6,231,561 B1 | 5/2001 | Frazier et al. |
| 6,238,415 B1 | 5/2001 | Sepetka et al. |
| 6,251,128 B1 | 6/2001 | Knopp et al. |
| 6,270,515 B1 | 8/2001 | Linden et al. |
| 6,283,935 B1 | 9/2001 | Laufer et al. |
| 6,287,317 B1 | 9/2001 | Makower et al. |
| 6,290,674 B1 | 9/2001 | Roue et al. |
| 6,290,699 B1 | 9/2001 | Hall et al. |
| 6,292,700 B1 | 9/2001 | Morrison et al. |
| 6,306,424 B1 | 10/2001 | Vyakarnam et al. |
| 6,312,446 B1 | 11/2001 | Huebsch et al. |
| 6,325,798 B1 | 12/2001 | Edwards et al. |
| 6,328,727 B1 | 12/2001 | Frazier et al. |
| 6,336,926 B1 | 1/2002 | Goble |
| 6,338,726 B1 | 1/2002 | Edwards et al. |
| 6,338,731 B1 | 1/2002 | Laufer et al. |

(56) References Cited

U.S. PATENT DOCUMENTS

| | | |
|---|---|---|
| 6,352,561 B1 | 3/2002 | Leopold et al. |
| 6,355,052 B1 | 3/2002 | Neuss et al. |
| 6,364,853 B1 | 4/2002 | French et al. |
| 6,364,876 B1 | 4/2002 | Erb et al. |
| 6,364,878 B1 | 4/2002 | Hall |
| 6,368,340 B2 | 4/2002 | Malecki et al. |
| 6,375,671 B1 | 4/2002 | Kobayashi et al. |
| 6,379,368 B1 | 4/2002 | Corcoran et al. |
| 6,398,779 B1 | 6/2002 | Buysse et al. |
| 6,402,772 B1 | 6/2002 | Amplatz et al. |
| 6,419,669 B1 | 7/2002 | Frazier et al. |
| 6,423,119 B1 | 8/2002 | Saadat |
| 6,430,446 B1 | 8/2002 | Knowlton |
| 6,432,119 B1 | 8/2002 | Saadat |
| 6,436,088 B2 | 8/2002 | Frazier et al. |
| 6,440,152 B1 | 8/2002 | Gainor et al. |
| 6,458,100 B2 | 10/2002 | Roue et al. |
| 6,461,327 B1 | 10/2002 | Addis et al. |
| 6,488,706 B1 | 12/2002 | Solymar |
| 6,494,881 B1 | 12/2002 | Bales et al. |
| 6,503,247 B2 | 1/2003 | Swartz et al. |
| 6,527,767 B2 | 3/2003 | Wang et al. |
| 6,527,786 B1 | 3/2003 | Davis et al. |
| 6,540,742 B1 | 4/2003 | Thomas et al. |
| 6,544,260 B1 | 4/2003 | Markel et al. |
| 6,551,303 B1 | 4/2003 | Van Tessel et al. |
| 6,551,344 B2 | 4/2003 | Thill |
| 6,558,375 B1 | 5/2003 | Sinofsky et al. |
| 6,558,385 B1 | 5/2003 | McClurken et al. |
| 6,582,430 B2 | 6/2003 | Hall |
| 6,596,013 B2 | 7/2003 | Yang et al. |
| 6,616,655 B1 | 9/2003 | Falwell et al. |
| 6,623,508 B2 | 9/2003 | Shaw et al. |
| 6,626,901 B1 | 9/2003 | Treat et al. |
| 6,632,223 B1 | 10/2003 | Keane |
| 6,634,878 B1 | 10/2003 | Bernardi et al. |
| 6,641,579 B1 | 11/2003 | Bernardi et al. |
| 6,650,923 B1 | 11/2003 | Lesh et al. |
| 6,652,517 B1 | 11/2003 | Hall et al. |
| 6,656,206 B2 | 12/2003 | Corcoran et al. |
| 6,659,105 B2 | 12/2003 | Burbank et al. |
| 6,666,861 B1 | 12/2003 | Grabek |
| 6,666,863 B2 | 12/2003 | Wentzel et al. |
| 6,673,068 B1 | 1/2004 | Berube |
| 6,673,090 B2 | 1/2004 | Root et al. |
| 6,676,656 B2 | 1/2004 | Sinofsky |
| 6,701,176 B1 | 3/2004 | Halperin et al. |
| 6,702,835 B2 | 3/2004 | Ginn |
| 6,709,432 B2 | 3/2004 | Ferek-Patric |
| 6,712,804 B2 | 3/2004 | Roue et al. |
| 6,712,815 B2 | 3/2004 | Sampson et al. |
| 6,712,836 B1 | 3/2004 | Berg et al. |
| 6,723,092 B2 | 4/2004 | Brown et al. |
| 6,730,081 B1 | 5/2004 | Desai |
| 6,735,532 B2 | 5/2004 | Freed et al. |
| 6,743,184 B2 | 6/2004 | Sampson et al. |
| 6,743,197 B1 | 6/2004 | Edwards |
| 6,755,822 B2 | 6/2004 | Reu et al. |
| 6,764,486 B2 | 7/2004 | Natale |
| 6,770,070 B1 | 8/2004 | Balbierz |
| 6,776,780 B2 | 8/2004 | Mulier et al. |
| 6,780,183 B2 | 8/2004 | Jimenez, Jr. et al. |
| 6,796,981 B2 | 9/2004 | Wham et al. |
| 6,802,843 B2 | 10/2004 | Truckai et al. |
| 6,805,130 B2 | 10/2004 | Tasto et al. |
| 6,813,520 B2 | 11/2004 | Truckai et al. |
| 6,821,273 B2 | 11/2004 | Mollenauer |
| 6,913,579 B2 | 7/2005 | Truckai et al. |
| 6,939,348 B2 | 9/2005 | Malecki et al. |
| 7,165,552 B2 | 1/2007 | Deem et al. |
| 9,259,267 B2 | 2/2016 | Forde |
| 9,510,902 B2* | 12/2016 | Parsonage ........ A61B 18/1492 |
| 2001/0014800 A1 | 8/2001 | Frazier et al. |
| 2001/0034537 A1 | 10/2001 | Shaw et al. |
| 2001/0037129 A1 | 11/2001 | Thill |
| 2001/0039435 A1 | 11/2001 | Roue et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0010481 A1 | 1/2002 | Jayaraman |
| 2002/0026094 A1 | 2/2002 | Ross |
| 2002/0029048 A1 | 3/2002 | Miller |
| 2002/0032462 A1 | 3/2002 | Houser et al. |
| 2002/0035374 A1 | 3/2002 | Borillo et al. |
| 2002/0052572 A1 | 5/2002 | Franco et al. |
| 2002/0096183 A1 | 7/2002 | Stevens et al. |
| 2002/0111645 A1 | 8/2002 | Wang et al. |
| 2002/0111647 A1 | 8/2002 | Khairkhahan et al. |
| 2002/0129819 A1 | 9/2002 | Feldman et al. |
| 2002/0183786 A1 | 12/2002 | Girton |
| 2002/0183787 A1 | 12/2002 | Wahr et al. |
| 2003/0028213 A1 | 2/2003 | Thill et al. |
| 2003/0045893 A1 | 3/2003 | Ginn |
| 2003/0045901 A1 | 3/2003 | Opolski |
| 2003/0050665 A1 | 3/2003 | Ginn |
| 2003/0069575 A1* | 4/2003 | Chin ................ A61B 18/1492 606/41 |
| 2003/0073979 A1 | 4/2003 | Naimark et al. |
| 2003/0088242 A1 | 5/2003 | Prakash et al. |
| 2003/0100920 A1 | 5/2003 | Akin et al. |
| 2003/0109778 A1 | 6/2003 | Rashidi |
| 2003/0139819 A1 | 7/2003 | Beer et al. |
| 2003/0144694 A1 | 7/2003 | Chanduszko et al. |
| 2003/0181945 A1 | 9/2003 | Opolsiki et al. |
| 2003/0191495 A1 | 10/2003 | Ryan et al. |
| 2003/0191526 A1 | 10/2003 | Van Tassel et al. |
| 2003/0195530 A1 | 10/2003 | Thill |
| 2003/0195531 A1 | 10/2003 | Gardiner et al. |
| 2003/0204203 A1 | 10/2003 | Khairkhahan et al. |
| 2003/0208232 A1 | 11/2003 | Blaeser et al. |
| 2004/0044361 A1 | 3/2004 | Frazier et al. |
| 2004/0049207 A1 | 3/2004 | Goldfarb et al. |
| 2004/0092973 A1 | 5/2004 | Chanduszko et al. |
| 2004/0143277 A1 | 7/2004 | Marino et al. |
| 2004/0143291 A1 | 7/2004 | Corcoran et al. |
| 2004/0143293 A1 | 7/2004 | Marino et al. |
| 2004/0143294 A1 | 7/2004 | Corcoran et al. |
| 2004/0192973 A1 | 9/2004 | Liang et al. |
| 2004/0193147 A1 | 9/2004 | Malecki et al. |
| 2004/0193239 A1 | 9/2004 | Falwell et al. |
| 2004/0215187 A1 | 10/2004 | Burbank et al. |
| 2004/0220596 A1 | 11/2004 | Frazier et al. |
| 2004/0220610 A1 | 11/2004 | Kreidler et al. |
| 2004/0230185 A1 | 11/2004 | Malecki et al. |
| 2004/0243122 A1 | 12/2004 | Auth et al. |
| 2004/0254572 A1 | 12/2004 | McIntyre et al. |
| 2004/0267191 A1 | 12/2004 | Gifford et al. |
| 2004/0267306 A1 | 12/2004 | Blaeser et al. |
| 2005/0021016 A1 | 1/2005 | Malecki et al. |
| 2005/0034735 A1 | 2/2005 | Deem et al. |
| 2005/0070887 A1 | 3/2005 | Taimisto et al. |
| 2005/0080406 A1 | 4/2005 | Malecki et al. |
| 2005/0125032 A1 | 6/2005 | Whisenant et al. |
| 2005/0131401 A1 | 6/2005 | Malecki et al. |
| 2006/0027241 A1 | 2/2006 | Malecki et al. |
| 2006/0074410 A1 | 4/2006 | Malecki et al. |
| 2006/0206189 A1 | 9/2006 | Furst et al. |
| 2006/0241581 A1 | 10/2006 | Malecki et al. |
| 2006/0241582 A1 | 10/2006 | Malecki et al. |
| 2006/0241583 A1 | 10/2006 | Malecki et al. |
| 2006/0241584 A1 | 10/2006 | Malecki et al. |
| 2006/0247612 A1 | 11/2006 | Malecki et al. |
| 2006/0271030 A1 | 11/2006 | Francis et al. |
| 2006/0271040 A1 | 11/2006 | Horne et al. |
| 2006/0271089 A1* | 11/2006 | Alejandro ......... A61B 17/0057 606/192 |
| 2006/0276779 A1 | 12/2006 | Malecki et al. |
| 2006/0276846 A1 | 12/2006 | Malecki et al. |

(56) References Cited

U.S. PATENT DOCUMENTS

| | | |
|---|---|---|
| 2007/0010806 A1 | 1/2007 | Malecki et al. |
| 2007/0066864 A1 | 3/2007 | Forde |

FOREIGN PATENT DOCUMENTS

| | | |
|---|---|---|
| EP | 1013227 A2 | 6/2000 |
| EP | 1046375 A1 | 10/2000 |
| EP | 1222897 A2 | 7/2002 |
| EP | 750905 B1 | 1/2003 |
| GB | 2407985 A | 5/2005 |
| WO | WO-199513111 A1 | 5/1995 |
| WO | WO-199625179 A1 | 8/1996 |
| WO | WO-199629946 A1 | 10/1996 |
| WO | WO-199631157 A1 | 10/1996 |
| WO | WO-1999629946 A1 | 10/1996 |
| WO | WO-199728744 A1 | 8/1997 |
| WO | WO-199839063 A1 | 9/1998 |
| WO | WO-199905977 A1 | 2/1999 |
| WO | WO-199918862 A1 | 4/1999 |
| WO | WO-199918864 A1 | 4/1999 |
| WO | WO-199918870 A1 | 4/1999 |
| WO | WO-199918871 A1 | 4/1999 |
| WO | WO-200018331 A2 | 4/2000 |
| WO | WO-200027292 A1 | 5/2000 |
| WO | WO-200074555 A2 | 12/2000 |
| WO | WO-2000074555 A2 | 12/2000 |
| WO | WO-200121247 A1 | 3/2001 |
| WO | 2001030266 A1 | 5/2001 |
| WO | WO-200130267 A1 | 5/2001 |
| WO | WO-200130268 A1 | 5/2001 |
| WO | WO-200149185 A1 | 7/2001 |
| WO | WO-200217809 A1 | 3/2002 |
| WO | WO-2002024106 A2 | 3/2002 |
| WO | WO-2003022159 A1 | 3/2003 |
| WO | WO-2003026525 A1 | 4/2003 |
| WO | WO-2003059152 A2 | 7/2003 |
| WO | WO-2003061481 A1 | 7/2003 |
| WO | WO-2003073944 A1 | 9/2003 |
| WO | WO-2003077733 A2 | 9/2003 |
| WO | WO-2004086944 A2 | 10/2004 |
| WO | WO-2004086951 A2 | 10/2004 |
| WO | WO-2005070316 A1 | 8/2005 |
| WO | WO-2005070491 A2 | 8/2005 |
| WO | WO-2005115231 A1 | 12/2005 |

OTHER PUBLICATIONS

De Ponti, R. et al, Trans-septal Catheterization for Radiofrequency Catheter Ablation of Cardiac Arrhythmias, The European Society of Cardiology, 19:943-950 (1998).

Hanson, James et al, "Metals That Remember", Science 81, 44-47 June.

International Search Report for International App. No. PCT/US2006/047479, dated Aug. 28, 2007 (6 pgs).

International Search Report for International Application No. PCT/US2006/034496, dated Jan. 26, 2007.

Kramer, Paul M.D., "PFO and Stroke: The Hidden Connection", Endovascular Today.

Lavergne et al "Transcatheter Radiofrequency Ablation of Atrial Tissue Using a Suction Catheter", PACE, vol. 12: 177-186, Jan. Part II 1989.

Protsenko et al, "Electrosurgical Tissue Resection: A Numerical and Experimental Study", Proceedings of SPIE, vol. 4954:64-70, (2003).

Ruiz et al, "The Puncture Technique: A New Method for Transcatheter Closure of Patent Foramen Ovale", Catherization and Cardiovascular Interventions, 53:369-372 (2001).

Sommer et al, "New Transseptal Puncture Technique for Transcatheter Closure of Patent Foramen Ovale", Mount Sinai Medical Center, Jun. 2002.

Stockel "Nitinol Medical Devices and Implants" SMST-2000 Conference Proceedings, 531-541 (2001).

Szili-Torok, "Transseptal Left Heart Catheterisation guided by Intracardiac Echocardiography", Heart 86:e11 (2001).

Written Opinion of the International Searching Authority for International Application No. PCT/US2006/034496, dated Jan. 26, 2007 (7 pages).

Written Opinion of the Searching Authority for International App. No. PCT/US2006/047479, dated Aug. 28, 2007 (8 pgs).

* cited by examiner

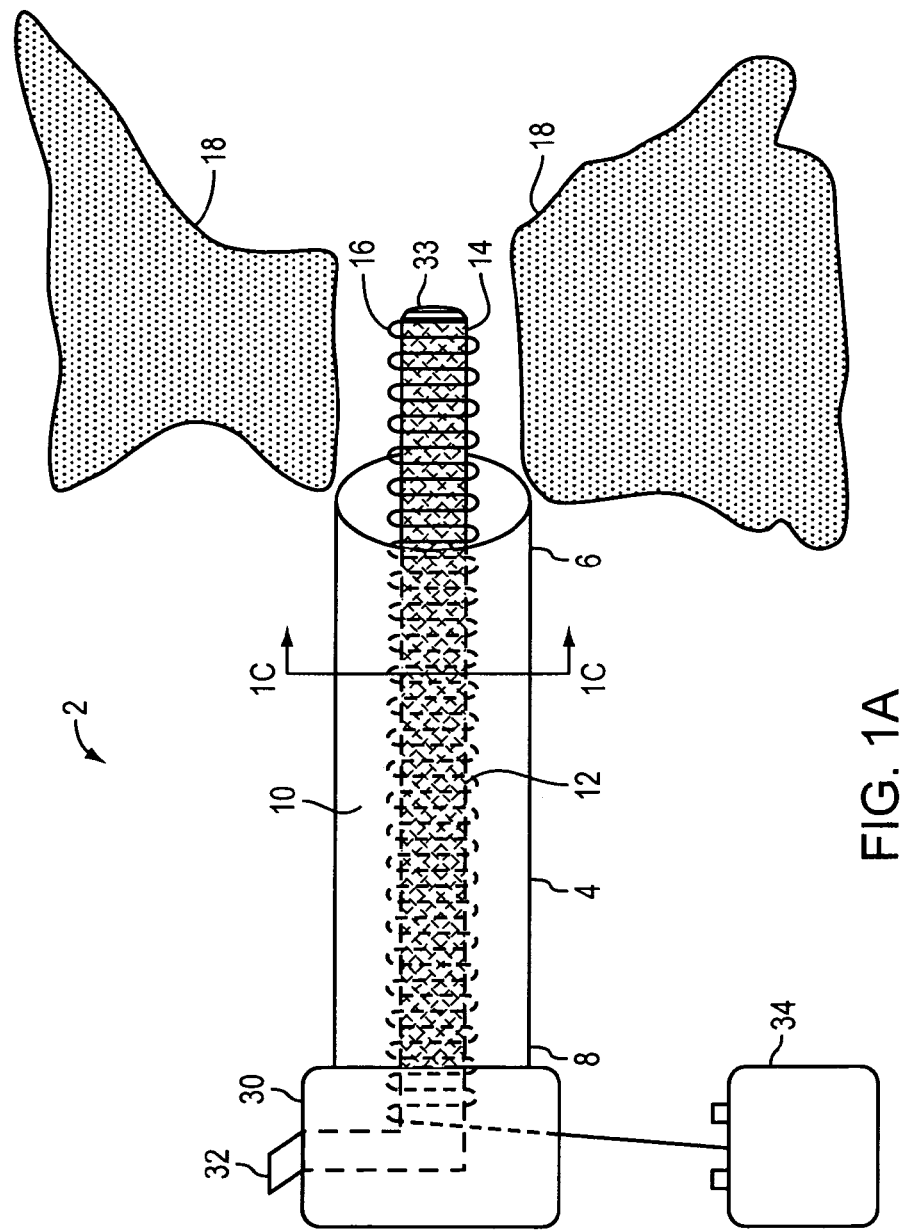

DEVICES AND METHODS FOR TREATING CARDIAC TISSUE

CROSS-REFERENCE TO RELATED APPLICATIONS

This application is a continuation application of U.S. application Ser. No. 11/516,144 filed Sep. 6, 2006, now issued as U.S. Pat. No. 9,259,267; which claims the benefit under 35 USC § 119(e) to U.S. Application Ser. No. 60/734,588 filed Nov. 8, 2005 and to U.S. Application Ser. No. 60/714,374 filed Sep. 6, 2005. The disclosure of each of the prior applications is considered part of and is incorporated by reference in the disclosure of this application.

BACKGROUND OF THE INVENTION

Field of the Invention

The invention generally relates to devices and related methods for treating cardiac tissue. More particularly, the invention features devices and methods of using devices comprising at least two different interwoven materials wherein at least one of the materials is an energy transferring material.

Background Information

The human heart is divided into four compartments or chambers. The left and right atria are located in the upper portion of the heart and the left and right ventricles are located in the lower portion of the heart. The left and right atria are separated from each other by a muscular wall, the interatrial septum, while the ventricles are separated by the interventricular septum.

Either congenitally or by acquisition, abnormal openings, holes, or shunts can occur between the chambers of the heart or the great vessels, causing blood to inappropriately flow there through. Such deformities are usually congenital and originate during fetal life when the heart forms from a folded tube into a four chambered, two-unit system. The septal deformities result from the incomplete formation of the septum, or muscular wall, between the chambers of the heart and can cause significant morbidity.

One such septal deformity or defect, a patent foramen ovale (PFO), is a persistent, one-way, usually tunnel shaped, flap-like opening in the wall between the right atrium and left atrium of the heart. Since left atrial pressure is normally higher than right atrial pressure, the flap typically stays closed. Under certain conditions, however, right atrial pressure exceeds left atrial pressure, creating the possibility for right to left shunting that can allow blood clots to enter the systemic circulation. This is particularly problematic for patients who are prone to forming venous thrombi, such as those with deep vein thrombosis or clotting abnormalities. Patients with a PFO may be prone to a cerebrovascular accident known as a stroke.

Moreover, certain patients are prone to atrial arrhythmias (i.e., abnormal heart rhythms which can cause the heart to pump less effectively). In a common such abnormality, atrial fibrillation, the two upper chambers of the heart (i.e., the left atria and the right atria), quiver instead of beating in coordination with other cardiac chambers. Because the atria do not beat and empty cleanly during atrial fibrillation, blood can stagnate on the walls and form clots that can then pass through the heart and into the brain, causing a stroke or a transient ischemic attack. These clots typically form in a cul-de-sac in the heart called the left atrial appendage due to its tendency to have low or stagnant flow.

Nonsurgical (i.e., percutaneous) tissue treatment and closure of a patent foramen ovale and similar cardiac openings, such as an atrial septal defect or a ventricular septal defect, as well as obliteration of a left atrial appendage, can be achieved using a variety of mechanical devices that are introduced via an artery into a large peripheral vessel, e.g., the femoral vein. These devices typically consist of a structural framework with a scaffold material attached thereto. Currently available devices, however, are often complex to manufacture, are inconsistent in performance, require a technically complex implantation procedure, lack anatomic conformability, and lead to complications (e.g., thrombus formation, chronic inflammation, residual leaks, perforations, device fractures, and conduction system disturbances).

Improved devices, systems, and related methods for treating cardiac tissue and/or closing cardiac openings, such as, for example, a patent foramen ovale, and for obliterating cardiac cul-de-sacs, such as, for example, a left atrial appendage, are therefore needed.

SUMMARY OF THE INVENTION

The present invention provides devices and related methods for treating cardiac tissue. In one aspect, the invention features a device for treating cardiac tissue. The device comprises a first sheath comprising a distal end, a proximal end and a lumen extending between the distal end and proximal end of the sheath. At least one elongated member is slidably disposed within the lumen of the sheath, and the elongated member is comprised of a first material and a second material. The first material is substantially non-conductive. while the second material is an energy transferring material. At least a portion of the second material is interwoven with at least a portion of the first material.

In one embodiment, the second material comprises copper, gold, metal, platinum, silver, iron, lithium, cobalt, nickel, chromium or a combination thereof, while in another embodiment the second material comprises an energy transferring ceramic or glass material. In another embodiment according to this aspect of the invention, the energy to be transferred includes electromagnetic energy, such as, for example, microwave, infrared, visible light waves, ultraviolet light waves, x-ray, gamma ray, or cosmic ray. In a further embodiment, the electromagnetic energy comprises radio frequency energy.

According to one embodiment, at least a portion of the elongated member comprises a straight wire or bristles, while in another embodiment, the second material is disposed on a filament. In another embodiment, at least a portion of the elongated member comprises a sleeve, and in an additional embodiment, at least a portion of the elongated member comprises a braid, coil, knot, spiral or zigzag. Alternatively, in yet another embodiment, at least a portion of the elongated member comprises a tube or a cone. In further embodiments, the elongated member comprises a lumen, and a negative force such as a negative pressure or vacuum is applied to the lumen of the elongated member. In other embodiments of the invention, a negative force is applied to the lumen of the sheath, while in a further embodiment the sheath is joined to a vacuum source.

In one embodiment, the device comprises a second sheath comprising a lumen for slidably receiving the first sheath. In additional embodiments, a negative pressure such as a vacuum is applied to the second sheath. In another embodiment, the second sheath is joined to a vacuum source. In a further embodiment, the second sheath is axially disposed within the lumen of the first sheath. In an even further embodiment, the elongated member is slidably receivable within the second sheath, while in another embodiment, the second sheath is axially disposed within a lumen of the elongated member.

In another embodiment of the invention, the elongated member is operatively joined to an actuator. In one embodiment, movement of the actuator causes movement of the elongated member in an axial direction in relation to the sheath. In other embodiments, the sheath is operatively joined to an actuator.

In another embodiment, the elongated member comprises a distal end and a proximal end. In a further embodiment, the elongated member comprises a wire. The wire comprises an open ended loop, the loop comprising a hairpin turn, for example, at the distal end of the elongated member and two free ends at the proximal end of the elongated member. According to one embodiment, at least one free end of the wire is affixed to an actuator. In another embodiment, movement of the actuator in a distal direction unfurls a portion of the elongated member from the lumen of the sheath moving the distal end of the elongated member even further in the distal direction. In a further embodiment, movement of the elongated member in the distal direction places at least a portion of the second material in contact with the cardiac tissue in need of treatment. In yet a further embodiment, movement of the actuator in a proximal direction retracts a portion of the elongated member inside the lumen of the sheath and moves the distal end of the elongated member in the proximal direction.

In another embodiment of the invention, the elongated member comprises a sleeve comprising an exterior surface and an interior surface. In one embodiment, the exterior surface of the sleeve is affixed to an actuator. In a particular embodiment, the sleeve comprises a first position in which a portion of the elongated member comprising the second material interwoven with the first material is located on the interior surface of the sleeve. In a further embodiment, movement of the actuator in a proximal direction transitions the sleeve into a second position wherein at least a portion the interwoven second material is located on the exterior surface of the sleeve.

Another embodiment of the invention features the interior surface of the sleeve affixed to an actuator. According to one embodiment, the sleeve comprises a first position in which the portion of the elongated member comprising the second material interwoven with the first material is located on the exterior surface of the sleeve. In another embodiment, movement of the actuator in a proximal direction transitions the sleeve into a second position wherein at least a portion the interwoven second material is located on the interior surface of the sleeve.

A further aspect of the invention includes a device for treating cardiac tissue. The device comprises at least one elongated member including a first material and a second material. The first material is a substantially non-conductive material, while the second material is an energy transferring material and at least a portion of the second material is interwoven with at least a portion of the first material. In one embodiment, the second material comprises copper, gold, metal, platinum, silver, iron, lithium, cobalt, nickel, chromium, or a combination thereof. In another embodiment, the second material comprises a glass or ceramic material.

Another aspect of the invention features a method for treating cardiac tissue. The method comprises the step of advancing a device to a position adjacent to cardiac tissue that is in need of treatment. The device includes a first sheath and at least one elongated member slidably disposed within a lumen of the sheath, the elongated member comprising a first material and a second material. The first material is substantially a non-conductive material. At least a portion of the second material is interwoven with at least a portion of the first material. The second material is capable of transferring energy from an energy source. The method further comprises the steps of advancing the elongated member through the lumen of the sheath wherein at least a portion of the second material comes into contact with the cardiac tissue in need of treatment, and applying the energy source to the second material to transfer energy to the cardiac tissue.

In one embodiment of this method of the invention, the elongated member comprises a wire, having an open ended loop. The loop comprises a hairpin turn at a distal end of the elongated member and two free ends at a proximal end of the elongated member. In another embodiment, at least one free end of the wire open-ended loop is operatively joined to an actuator. In a particular embodiment, movement of the actuator in the distal direction unfurls a portion of the elongated member from the lumen of the sheath, thereby moving the distal end of the elongated member in the distal direction. In an additional embodiment, the method further comprises the step of moving the actuator in the distal direction to place at least a portion of the second material in contact with the cardiac tissue in need of treatment. In a further embodiment, movement of the actuator in the proximal direction retracts a portion of the elongated member within the lumen of the sheath and moves the distal end of the elongated member in the proximal direction.

According to one embodiment, energy comprises microwave, infrared, visible light waves, ultraviolet light waves, x-ray, gamma ray, or cosmic ray. In another embodiment, the energy comprises radio frequency energy.

A further embodiment according to this aspect of the method of the invention comprises the step of attaching a vacuum source in communication with the lumen of the first sheath or the second sheath. The method of the invention can further comprise the step of applying a negative pressure to the lumen of the first sheath or the second sheath. In a further embodiment, the negative pressure is provided by a vacuum generating source, e.g., a pump.

In an additional embodiment, the device of the invention comprises a second sheath having a lumen wherein the first sheath is axially disposed within the second sheath. In one embodiment, the method comprises the step of applying a negative force, e.g., negative pressure to the lumen of the second sheath. In a further embodiment, the device comprises a second sheath having a lumen and the second sheath is axially disposed within the lumen of the first sheath. In a further embodiment, the elongated member is slidably receivable in the second sheath. Alternatively, the elongated member is fixed and the sheath is slidably moveable over the elongated member.

A further aspect of the invention features a method for treating cardiac tissue and comprises the step of advancing a device to a position adjacent to cardiac tissue in need of treatment. The device includes at least one elongated member comprising a first material and a second material. The first material is a substantially non-conductive material. The second material is an energy transferring material. At least a portion of the second material is interwoven with at least a portion of the first material, and the second material is capable of transferring energy from an energy source. This aspect also includes the steps of contacting at least a portion of the second material with the cardiac tissue in need of treatment, and transferring energy to the cardiac tissue in need of treatment.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1A is a schematic side view of a device for treating cardiac tissue, according to an illustrative embodiment of the invention.

DETAILED DESCRIPTION OF THE INVENTION

Figure 1B:
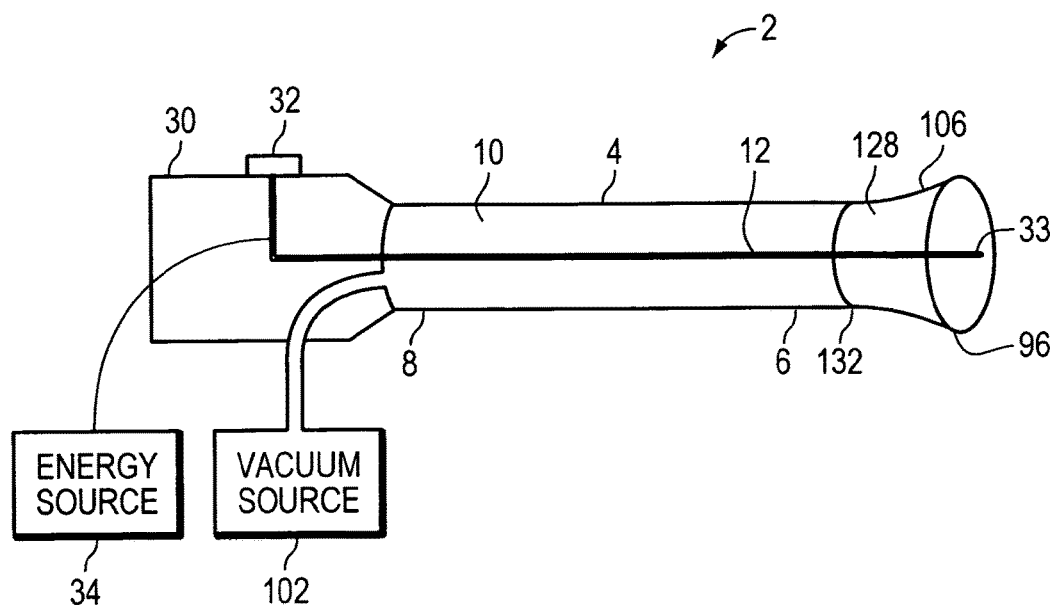
FIG. 1B is a schematic side view of a device for treating cardiac tissue including a vacuum source and vacuum cone according to another embodiment of the invention.

The present invention features devices and related methods for treating cardiac tissue. The cardiac tissue in need of treatment includes, for example, cardiac septa and tissue of the left and right atria. The invention is also useful in closing various cardiac openings, for example, a patent foramen ovale (PFO), an atrial septal defect, or a ventricular septal defect.

The present invention features systems and related methods for closing cardiac openings, such as, for example, a PFO, described below. Throughout the description, the terms proximal and distal refer to the position of elements relative to the operator of the exemplary apparatus. Proximal is that portion of the device closer to the operator and distal is that portion of the device further away from the operator.

FIG. 1A is a schematic side view of an exemplary device 2 for treating cardiac tissue 18, the device 2 comprising a sheath 4 having a distal end 6, a proximal end 8, and a lumen 10 that extends between the distal end 6 and proximal end 8 of the sheath 4, a handle 30, and an actuator 32 on the handle 30. The exemplary sheath 4 extends from a proximal end 8 at the handle 30 to a distal end 6. In one embodiment, shown in FIG. 1A, the device 2 further features at least one elongated member 12 slidably disposed within the lumen 10 of the sheath 4.

FIG. 1B illustrates yet another embodiment of the device 2 including a vacuum source 102. This embodiment may feature a cone 106 disposed at the distal end 6 of the sheath 4.

The vacuum source 102 is used to apply negative pressure through the vacuum cone 106 to stabilize the sheath 4 while delivering the elongated member 12 into, for example, a PFO tunnel. The vacuum applied to stabilize the sheath 4 may also have the advantage of collapsing the tunnel of the PFO. The lumen 128 of the vacuum cone 106 may be in communication with the lumen 10 of the sheath 4.

A cone, as used herein, means any tubular shape or any tubular shape with a flared end. In a preferred embodiment, the cone 106 includes a tube having a flared end, i.e., the diameter of the distal end 96 of the cone 106 is greater than the diameter of the proximal end 132 of the cone 106. The flare may begin at the proximal end 132 of the cone 106 and extend gradually to the distal end of the cone 106 as illustrated in FIG. 1B, or, alternatively, the flare may begin anywhere along the long axis of the cone 106 and extend to the distal end of the cone 106 (not shown). The distal end of the cone 106 may be circular, oval, U-shaped or any other shape suitable for interfacing with intracardiac tissue. According to the invention, the cone 106 and vacuum source 102 may or may not be present and the invention is not limited to an apparatus including a vacuum or other source of negative pressure. Furthermore, the cone 106 may be applied to the distal end of any sheath in the device and is not limited to the sheath illustrated.

With continued reference to FIG. 1B, in one embodiment, the cone 106 includes a single lumen 128 extending from the proximal end 132 of the cone 106 to the distal end of the cone 106. The lumen 128 of the cone 106 houses the elongated member 12 and may be in communication with the lumen 10 of the sheath 4. In one embodiment, the lumen 128 is in fluid communication with the lumen 10 of the sheath 4. Alternatively, the cone 106 has a plurality of lumens 128 (not shown). One of the plurality of lumens 128 houses the elongated member 12. At least one other of the plurality of lumens 128 is in fluid communication with the lumen 10 of the sheath 4.

Referring still to FIG. 1B, in a preferred embodiment, a vacuum source 102 is operatively joined to the lumen 10 of the sheath 4 to the lumen 128 of the cone 106.

With further reference to FIG. 1B, the elongated member 12 extends through the lumen 10 of sheath 4. In one embodiment, the distal end 33 of the elongated member 12 transitions from a first position, where the distal end 33 of the elongated member 12 is housed within the lumen 10 to a second position, where the distal end 33 of the elongated member 12 is positioned beyond the distal end of the sheath 4 or the distal end of the cone 106 in embodiments including a cone 106.

According to one embodiment of the invention, the elongated member 12 includes a first material 14 and a second material 16. In one embodiment, at least a portion of the second material 16 is interwoven with at least a portion of the first material 14. In a particular embodiment, at least the second material 16 interwoven with first material 14 is an energy transferring material that can transfer energy from an energy source 34 to, for example, adjacent cardiac tissue. The second material 16 may be in the form of a thread, filament cord, rope, ribbon, plate or sheet, for example. In yet another embodiment, the elongated member 12 is transitioned from within the sheath 4 to extend beyond the distal end 6 of the sheath 4 to place the distal end of the elongated member 12 including the second material 16 in direct contact or, alternatively in indirect contact, for example, through water or saline, with cardiac tissue 18 in need of treatment.

The elongated member 12 can be any shape depending on the intended use of the device 2 and/or the user's preference. In certain embodiments, the elongated member 12 comprises a straight wire or, alternatively, one or more bristles (not shown) at the distal end 33 of the elongated member 12. In another embodiment, the elongated member 12 comprises a sleeve. In other embodiments, the elongated member 12 comprises a braid, coil, knot, spiral or zigzag shape. Alternatively, the elongated member 12 can be in the shape of a tube or a cone. In certain embodiments, the elongated member 12 includes a lumen. In other embodiments, the device of the invention comprises two or more elongated members 12. Each elongated member 12 can be manipulated independently or in unison with the other(s) in the manner described below.

In a particular embodiment, the second material 16 may be positioned on one or more bristles or braided, coiled, knotted, spiral or zigzag or bonded with the first material 14 on the elongated member 12. For example, the first material 14 may be an insulator of the second material 16. Uninsulated portions of the second material 16 are contacted with the tissue in need of treatment. Alternatively, the elongated member 12 may include only the second material 16.

With respect to the material of the elongated member 12, by "interwoven" it is meant that at least a portion of the first material 14 and a portion of the second material 16 are connected closely by being in direct contact with each other, e.g., threaded, woven through or overlapping the other or indirect contact. By "direct contact" it is meant that at least a portion of the first material 14 and a portion of the second material 16 are physically touching each other. By "indirect contact" it is meant that at least a portion of the first material 14 and a portion of the second material 16 are in physical contact with a common object or common third material. By "threaded" it is meant that one material in the form of a thread or wire is physically passed into or through the other.

In one embodiment according to the invention, the first material 14 and the second material 16 of the elongated member are different compositions. According to one embodiment, the first material 14 comprises, for example, a polymer, such as a plastic, for example, nylon or polyester. The second material 16 comprises any material capable of transferring energy, for example, electromagnetic energy, from an energy source to a target tissue, for example, cardiac tissue. In one embodiment, the second material is, for example, copper, gold, metal, platinum, silver, iron, lithium, cobalt, nickel, chromium, glass, ceramic or a combination thereof. The electromagnetic energy transferred may be, for example, one of microwave, infrared, visible light waves, ultraviolet light waves, x-ray, gamma ray, laser energy, or cosmic ray. In a particular embodiment, the electromagnetic energy is radio frequency energy.

According to one embodiment of the invention, at least a portion of the second material 16 is interwoven with at least portion of the first material 14. For example, the materials 14, 16 can cross each other one or more times, be braided together, threaded through one another, twisted together, coiled together, woven through each other, and/or knotted together. Alternatively, the materials 14, 16, when placed adjacent to each other, can be collectively formed into the shape of a braid, coil, knot, spiral, zigzag, straight wire, or bristles. The material 14, 16 may be laminated or crimped together. The second material 16 extends from the energy source 34 to at least the distal end of the elongated member 12.

Referring now to FIG. 1A, another embodiment of the invention features the sheath 4 operatively joined to an actuator 32, positioned on, for example, a handle 30, wherein movement of the actuator 32 causes axial movement of the sheath 4 relative to the stationary elongated member 12. In another embodiment, the elongated member 12 is operatively joined to the actuator 32 wherein movement of the actuator causes axial movement of the elongated member 12 relative to the stationary sheath 4. In one embodiment, the actuator is a knob or a button.

Figure 1C:
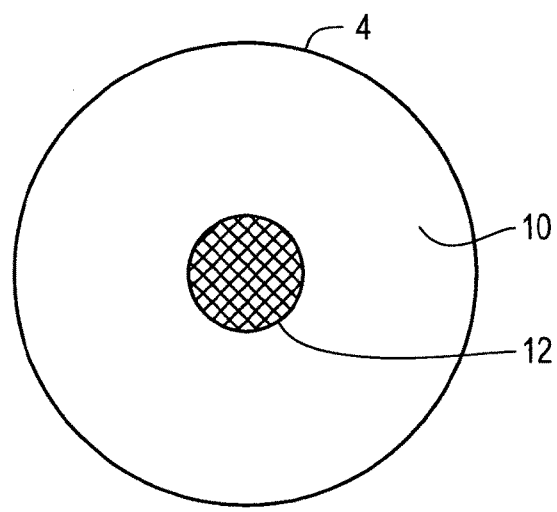
FIG. 1C is a schematic view of a cross section in FIG. 1A taken at 1B-1B.

FIG. 1C is a schematic view of a cross section in FIG. 1A taken at 1C-1C. As shown in FIG. 1C, one embodiment of the invention features the elongated member 12 located within the lumen 10 of the sheath 4.

Figure 2A:
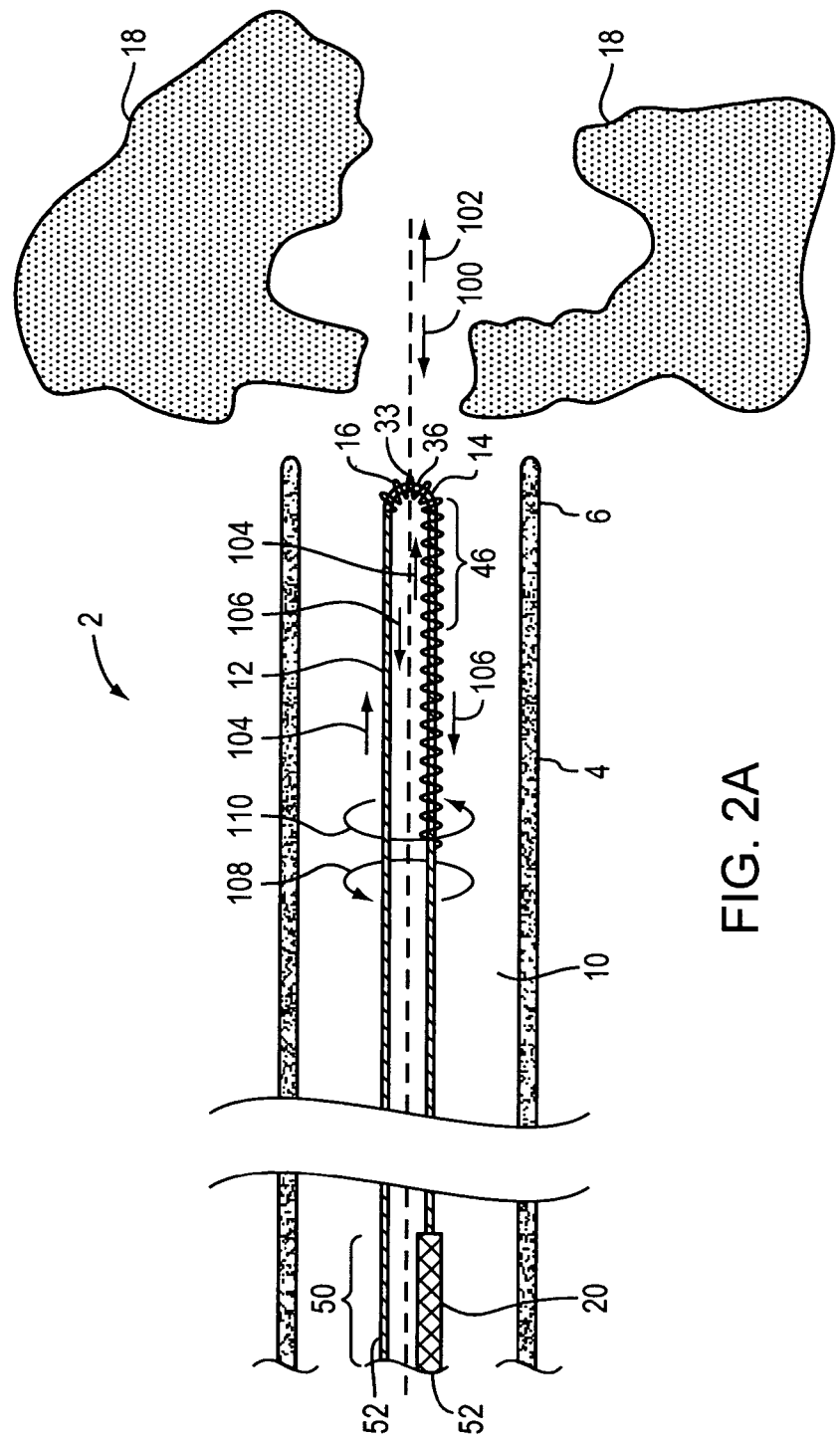
FIG. 2A is a partial cross-sectional view of a distal end of a device for treating cardiac tissue, the device comprising an elongated member retracted within a lumen of the sheath of the device, according to an illustrative embodiment of the invention.

FIG. 2A is a partial cross-sectional view of a distal end of a device 2 for treating cardiac tissue, the device 2 comprising an elongated member 12 retracted within a lumen 10 of the device 2 according to an illustrative embodiment of the invention. As shown in FIG. 2A, one embodiment features an elongated member 12 comprising a distal end 33 and a proximal end 50. According to the illustrative embodiment, the elongated member 12 is, for example, a single wire such as for example, a single braided wire comprising a hairpin turn 36 at the distal end 33 of the elongated member 12 to form an open loop configuration with the two free ends 52 of the wire located at the proximal end 50 of the elongated member 12. In one embodiment, the elongated member 12 is in the form of a wire that forms a closed loop configuration at the distal end 33 of the elongated member 12, with both of the ends 52 of the wire joined to each other or joined to a common object, for example, directly or indirectly to an actuator, at the proximal end 50 of the elongated member 12.

In one embodiment, the second material 16 follows the path of the first material 14 forming a bipolar device. Alternatively, the second material 16 partially follows the path of the first material 14, forming a unipolar device.

With continued reference to the embodiment shown in FIG. 2A, at least one end 52 of the wire is operatively joined to an object, for example, a carrying cable 20. According to one embodiment, the carrying cable 20 is connected to an actuator (not shown) such that actuation of the actuator effectuates movement of the cable 20 and the elongated member 12. In a particular embodiment, movement of the actuator causes the elongated member 12 to move axially in relation to the sheath 4, i.e., in a motion parallel to the sheath 4 (as indicated by direction arrows 100 and 102). In another embodiment, movement of the actuator causes the elongated member 12 to move in a circumferential motion, i.e., rotational movement of the circumference of the loop in one or more directions as indicated by arrows 108 and 110.

Figure 2B:
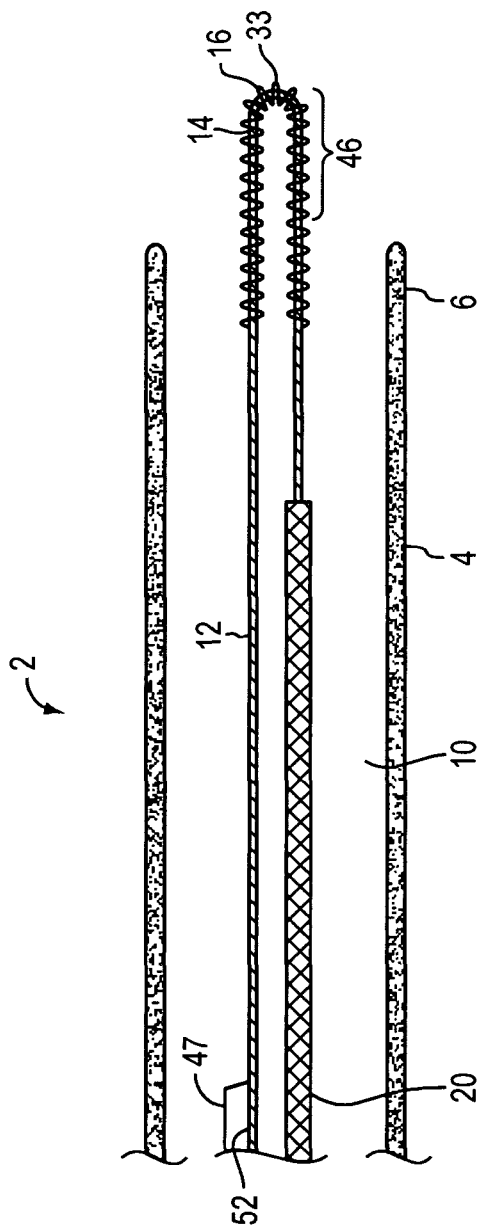
FIG. 2B is a partial cross-sectional view of the distal end of a device for treating cardiac tissue as illustrated in FIG. 2A, with the elongated member unfurled beyond the distal end of the sheath, according to an illustrative embodiment of the invention.

In a further embodiment, the one end 52 of the wire that is not joined to the cable 20 is fixed within the device 2. In another embodiment, as shown in FIG. 2B, axial movement of the cable 20 in the distal direction allows the elongated member 12 to unfurl from the lumen 10 of the sheath 4. By unfurl it is meant that the distal end portion 46 of the elongated member 12 moves in the distal direction to extend the length of the elongated member 12 from the proximal end 50 to the distal end 33 of the elongated member 12 while the end 52 remains stationary (similar to that of a bicycle chain, for example, with one end fixed) as indicated by direction arrows 104 and 106 in FIG. 2A, relative to the sheath 4. The distal end 33 of the unfurled elongated member 12 can be extended beyond the distal end 6 of the sheath 4. Alternatively, axial movement of the cable 20 in the proximal direction can allow the distal end 33 of the elongated member 12 to move in the proximal direction and retract the distal end 33 of the elongated member further inside the lumen 10 of the sheath 4.

Figure 2C:
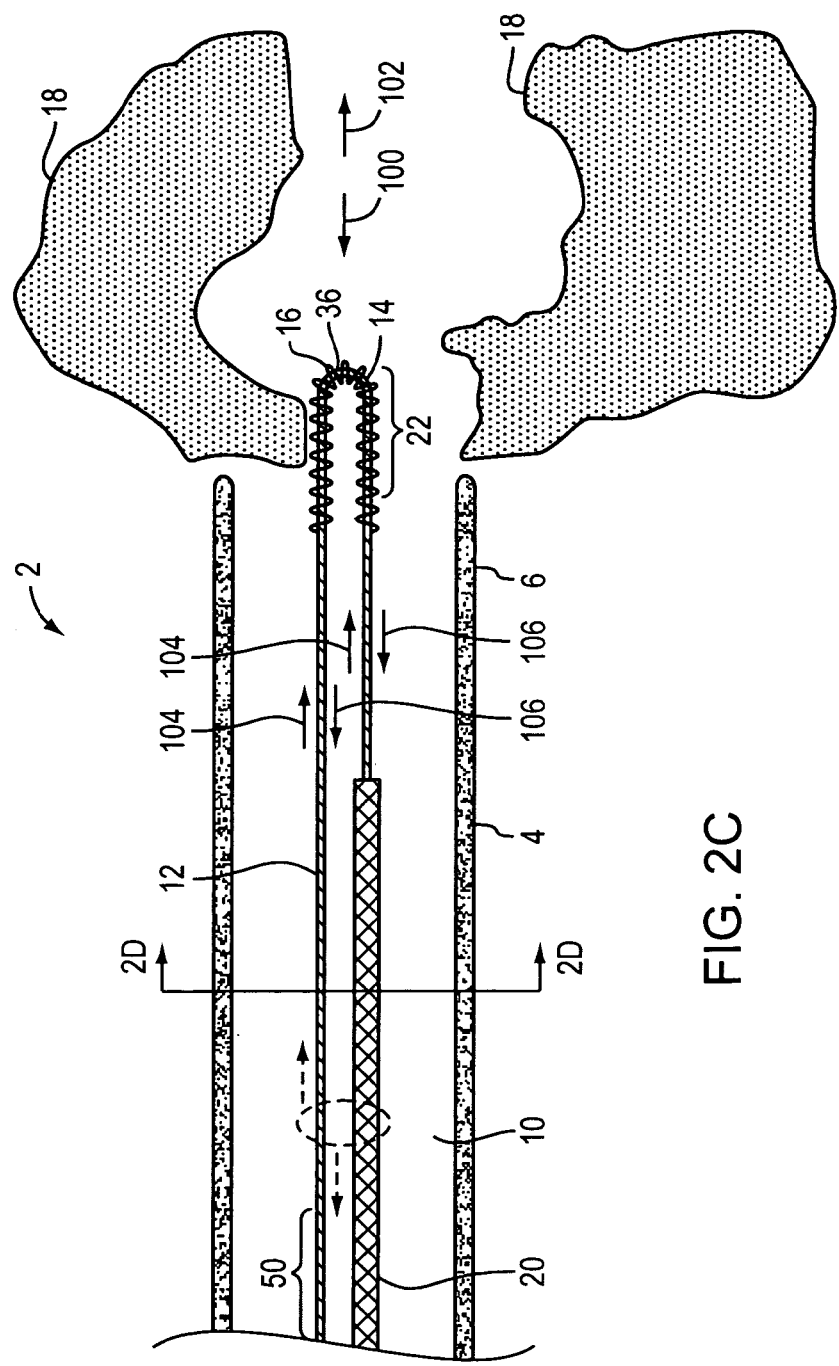
FIG. 2C is a partial cross-sectional view of the distal end of the device for treating cardiac tissue as illustrated in FIG. 2A, with the elongated member extended distally beyond the lumen of the sheath and in proximity to tissue in need of treatment, according to an illustrative embodiment of the invention.

FIG. 2C is a partial cross-sectional view of the distal end 6 of the device 2 for treating cardiac tissue 18 as illustrated in FIG. 2A, with the elongated member 12 extended distally beyond the lumen 10 of the sheath 4 and in proximity to tissue in need of treatment according to an illustrative embodiment of the invention. As illustrated in FIG. 2C, manipulation of the elongated member 12 according to each of the embodiments described above allows the portion 22 of the elongated member 12 comprising the first interwoven materials 14 and the second interwoven material 16 to be placed in a desired location within a patient's body. Energy is transferred from an energy source 34 to the second material 16 in contact with the target tissue 18 and from the second material 16 to the target tissue 18.

In a preferred embodiment, manipulation of the elongated member 12 carries the second material 16 into the PFO tunnel. Upon further manipulation of the elongated member 12, the distal end of the elongated member retracts proximally, and leaves the PFO tunnel, and the second material transfer energy to the septum tissue along the track, and therefore causes the target tissue to fuse together.

Figure 2D:
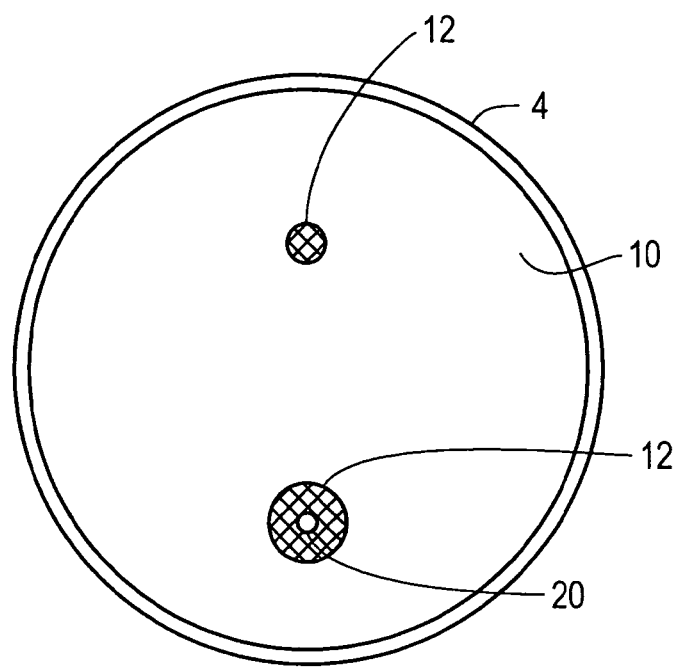
FIG. 2D is a schematic view of a cross section in FIG. 2C taken at 2D-2D.

FIG. 2D is a schematic view of a cross section in FIG. 2C taken at 2D-2D. As shown in FIG. 2D, according to the exemplary embodiment of FIG. 2C, the elongated member 12, for example, is a wire having a hairpin turn. One end of the wire is attached to the cable 20. The elongated member 12 is axially positioned within the lumen 10 of the sheath 4.

Figure 3A:
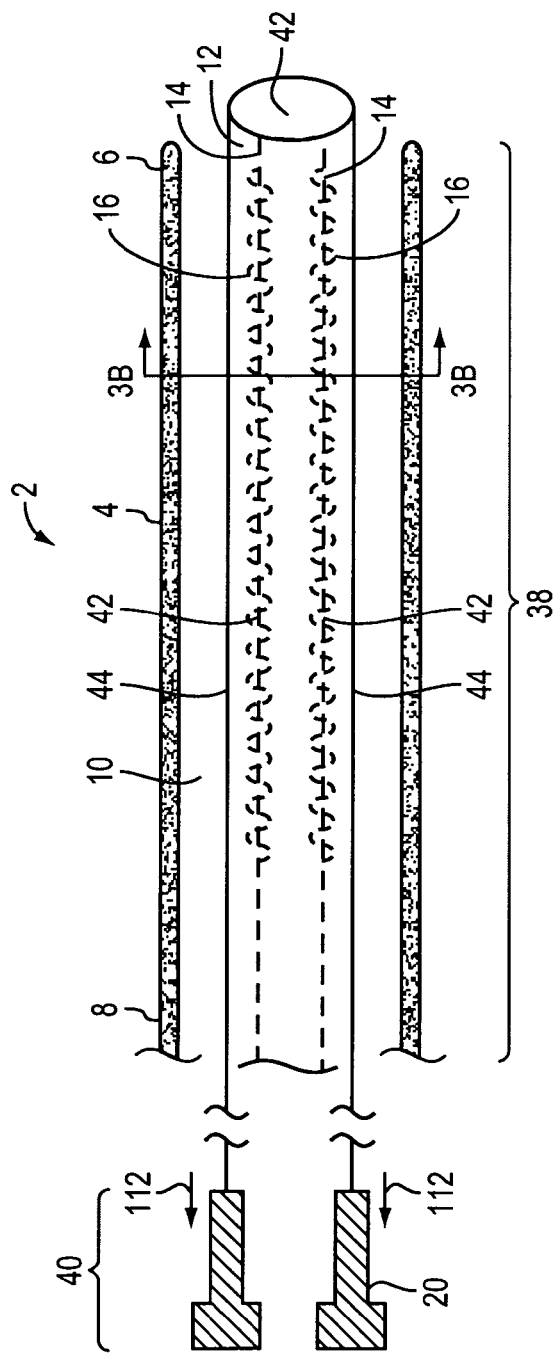
FIG. 3A is a partial cross-sectional view of a distal end and proximal end of a device for treating cardiac tissue, the device comprising an elongated member in the form of a sleeve and a cable for manipulating the elongated member, according to an illustrative embodiment of the invention.

FIG. 3A is a partial cross-sectional view of a distal end portion 38 of a device 2 for treating cardiac tissue, the device 2 comprising an elongated member 12 in the form of a sleeve and a cable 20 for manipulating the elongated member 12 according to an illustrative embodiment of the invention. According to one embodiment, the sleeve 12 comprises an interior surface 42 and an exterior surface 44.

In the embodiment shown in FIG. 3A, the portion of the elongated member 12 comprising the second material 16 interwoven with the first material 14 is located at least on the interior surface 42 of the sleeve 12.

Figure 3B:
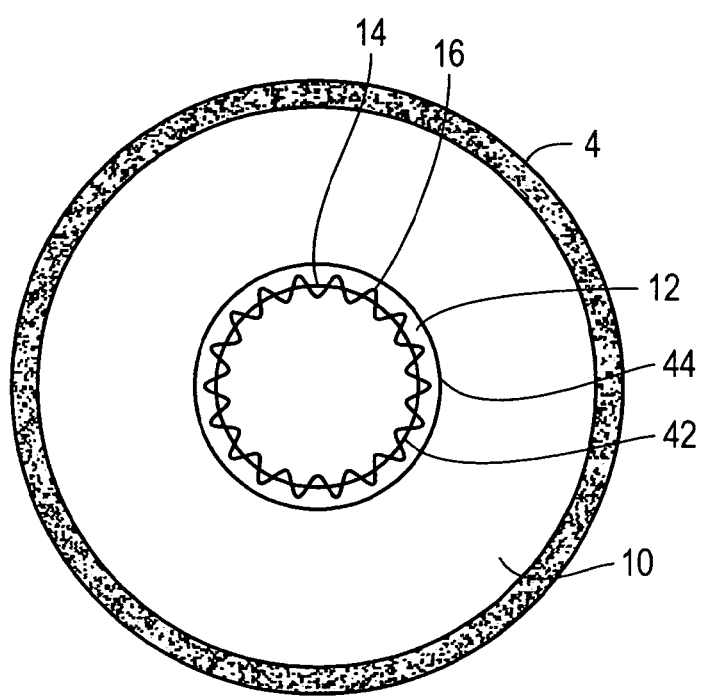
FIG. 3B is a schematic view of a cross section in FIG. 3A taken at 3B-3B.

FIG. 3B is a schematic view of a cross section in FIG. 3A taken at 3B-3B. In one embodiment, shown in FIG. 3B, the sleeve 12, located within the lumen 10 of the sheath 4, comprises an interior surface 42 and an exterior surface 44, wherein the portion of the sleeve 12 comprising the interwoven second material 16 is located on the interior surface 42 of the sleeve 12.

Figure 3C:
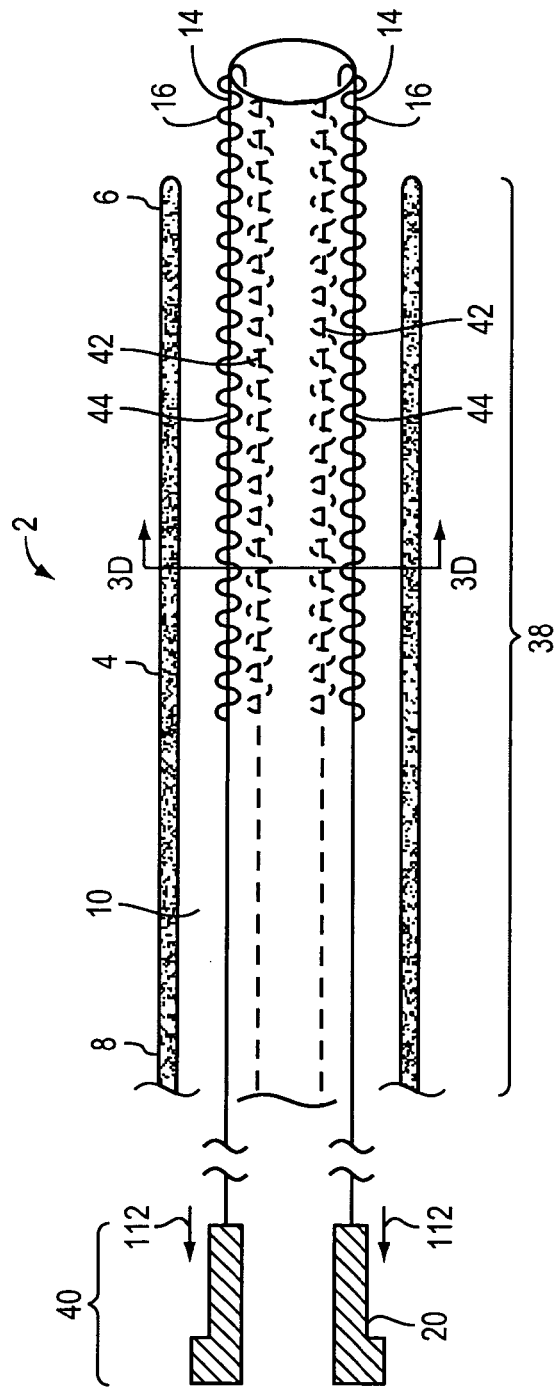
FIG. 3C is a partial cross-sectional view of the device illustrated in FIG. 3A after the elongated member is manipulated in the direction indicated by direction arrow 112 in FIG. 3A, according to an illustrative embodiment of the invention.

Referring now to the embodiment shown in FIG. 3A, the portion of the elongated member 12 comprising the second material 16 interwoven with the first material 14 is initially located on the interior surface 42 of the sleeve 12. According to one embodiment, the cable 20 is operatively joined to the exterior surface 44 of the sleeve 12. Referring now to FIG. 3C, axial movement of the cable 20 proximally in the direction indicated by direction arrow 112 lengthens the exterior surface 44 and shortens the interior surface 42 of the sleeve. At least a portion of the inner surface of the sleeve 12 becomes everted and at least a portion of the sleeve 12 comprising the interwoven second material 16 is relocated from the interior surface 42 to the exterior surface 44 of the sleeve 12. In one embodiment for treating cardiac tissue, the portion of the everted sleeve 12 comprising the interwoven second material 16 contacts the tissue in need of treatment when the second material 16 on the distal end of the sleeve 12 is extended beyond the distal end of the sheath 4, and electromagnetic energy from the energy source is transferred from the second material 16 to the tissue.

Alternatively, in another embodiment (not shown), the cable 20 is operatively joined to the interior surface 42 of the sleeve 12. Axial movement of the cable 20 in a distal direction lengthens the exterior surface 44 and shortens the interior surface 42 of the sleeve such that at least a portion of the interior surface 42 of the sleeve 12 becomes everted and at least a portion of the sleeve 12 comprising the interwoven second material 16 is relocated to the distal end of the sleeve 12 and the exterior surface 44 of the inverted sleeve 12. In one embodiment for treating cardiac tissues, the portion of the everted sleeve 12 comprising the interwoven second material 16 contacts the tissue in need of treatment and electromagnetic energy from the energy source is transferred from the second material 16 to the tissue.

Figure 3D:
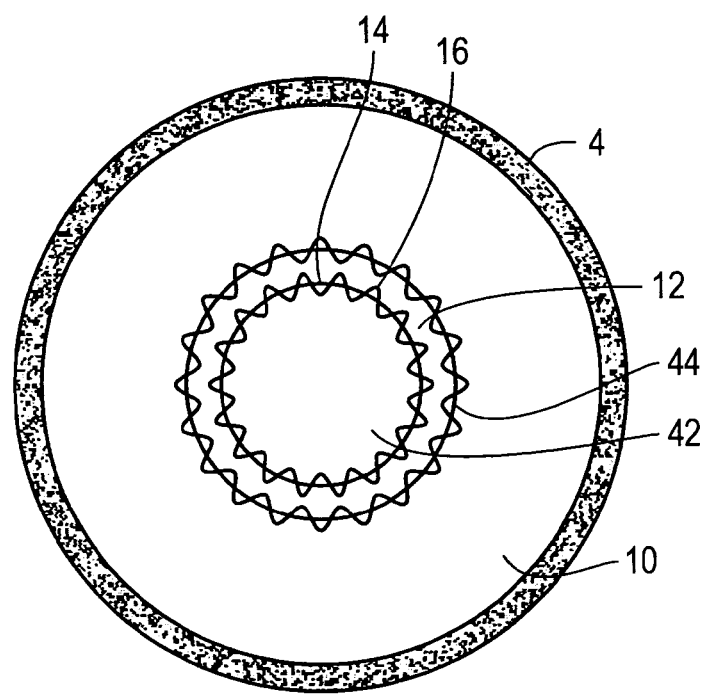
FIG. 3D is a schematic view of a cross section in FIG. 3C taken at 3D-3D.

FIG. 3D is a schematic view of a cross section in FIG. 3C taken at 3D-3D. In the exemplary embodiment, shown in FIG. 3D, the sleeve 12 is located within the lumen 10 of the sheath 4 and the portion of the sleeve 12 comprising the interwoven second material 16 is located on both the interior surface 42 and the exterior surface 44 of the inverted sleeve 12.

Referring now to FIGS. 3C and 3D, according to one embodiment of the invention, the sheath 4 of the device 2 moves relative to the sleeve 12 such that movement of the sheath 4 in the proximal direction exposes the sleeve 12 beyond the distal end of the sheath 4. In another embodiment, the sleeve 12 moves relative to the sheath 4, such that movement of the sleeve 12 in the distal direction exposes the sleeve 12 beyond the distal end of the sheath 4.

In further embodiments of the invention of the device 2, the proximal end 8 of the sheath 4 is coupled to a vacuum source to allow functional communication with the lumen 10 of the sheath 4. This configuration allows the user to apply negative pressure, i.e., suction, to the targeted cardiac tissue 18 as the distal end of the sheath 4 is applied to the tissue 18.

The negative pressure vacuum can be used to draw the cardiac tissue toward the second material 16. With the tissue in contact with the second material 16, energy transfers from the second material 16 directly to the tissue. In one embodiment, the negative pressure from the vacuum source is maintained while the energy is applied to the tissue.

Figure 4:
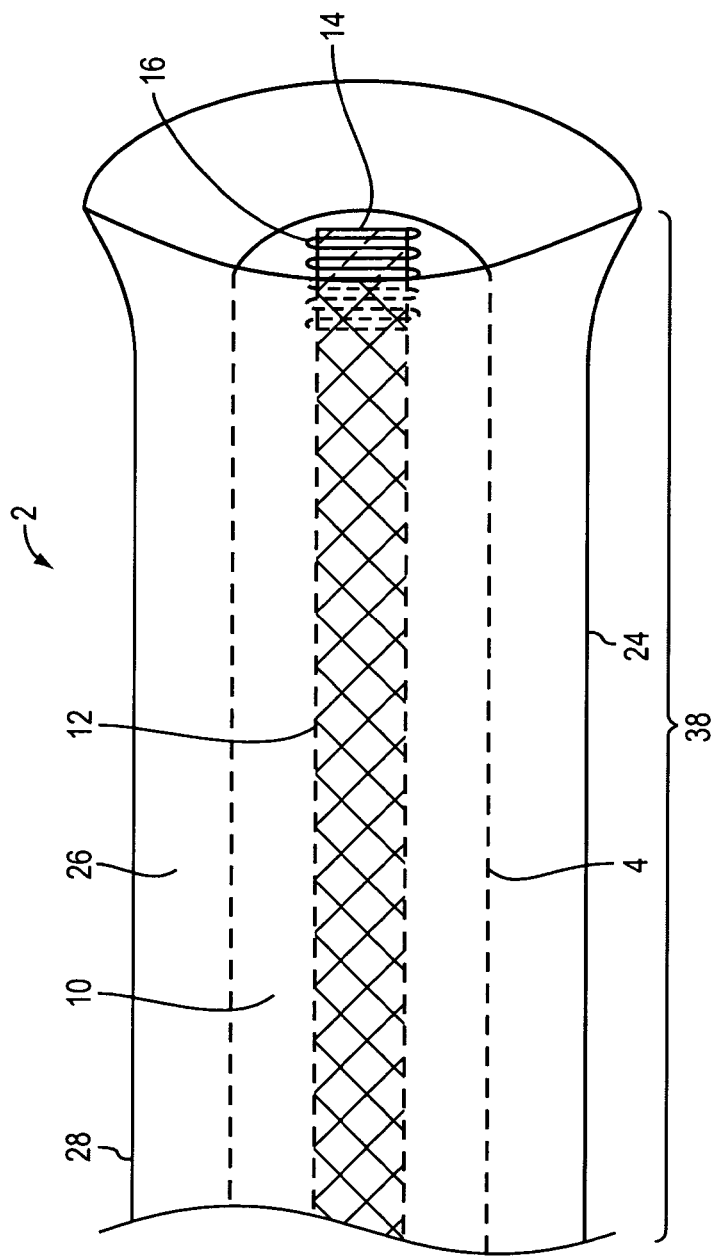
FIG. 4 is a schematic side view of a distal end of a device for treating cardiac tissue, the device comprising a first sheath, an elongated member and a second sheath surrounding the first sheath, according to an illustrative embodiment of the invention.

FIG. 4 is a schematic side view of a distal end 38 of a device 2 for treating cardiac tissue, the device 2 comprising a first sheath 4, an elongated member 12 and a second sheath 24 surrounding the first sheath 4 according to an illustrative embodiment of the invention. The elongated member 12 may be any one of the elongated members illustrated in FIG. 1A-1C, 2A-2D, or 3A-3D and described in the corresponding text. In one embodiment, as illustrated in FIG. 4, the lumen 26 of second sheath 24 surrounds the first sheath 4 and the first sheath 4 is located within the lumen 26 of the second sheath 24. In another embodiment, the second sheath 24 is functionally joined to a vacuum source, for example, at the proximal end 28 of the second sheath 24.

Figure 5:
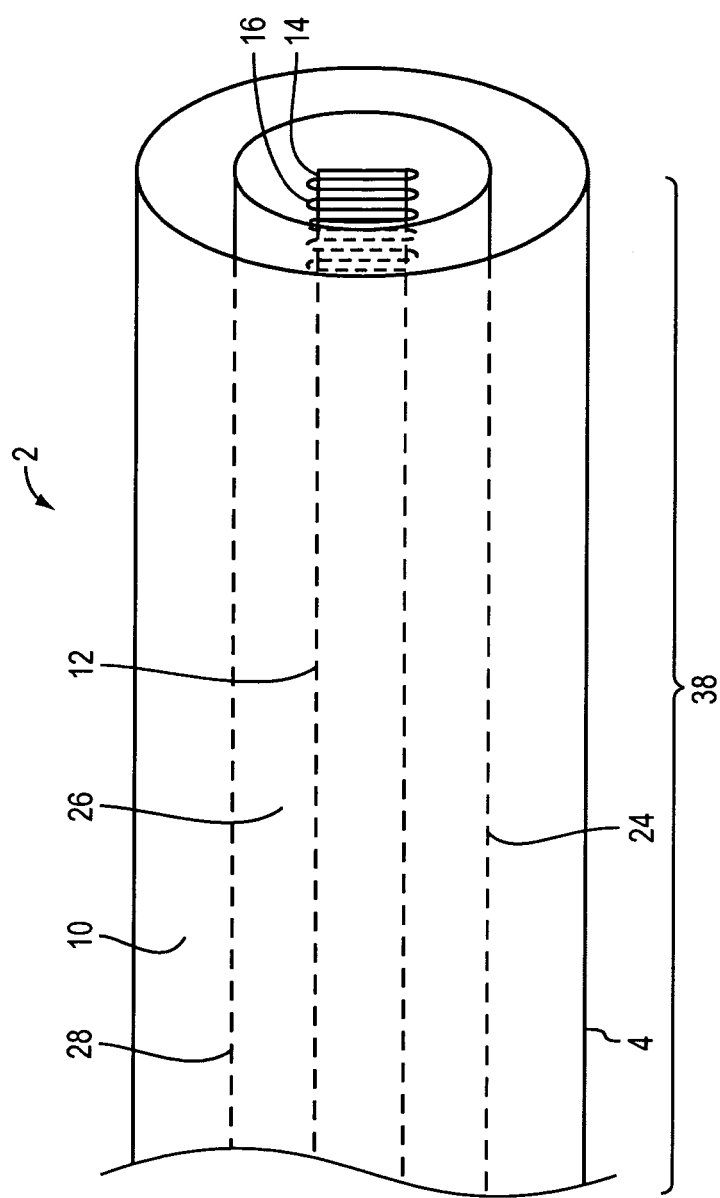
FIG. 5 is a schematic side view of a distal end of a device for treating cardiac tissue, the device comprising a first sheath, an elongated member and a second sheath within the lumen of the first sheath, according to an illustrative embodiment of the invention.

FIG. 5 is a schematic side view of a distal end 38 of a device 2 for treating cardiac tissue, the device comprising a first sheath 4, an elongated member 12 and a second sheath 24 within the lumen 10 of the first sheath 4, according to an illustrative embodiment of the invention. In one embodiment, as shown in FIG. 5, the second sheath 24 is axially positioned within the lumen 10 of the first sheath 4 and surrounds the elongated member 12 such that the elongated member 12 is located within the lumen 26 of the second sheath 24. In another embodiment (not shown), the second sheath 24 is within the lumen 10 of the first sheath 4 and adjacent to the elongated member 12. In one embodiment, the second sheath 24 is functionally joined to a vacuum source, at, for example, a proximal end 28 of the second sheath 24. In an even further embodiment (not shown), the elongated member 12 comprises a lumen, and the second sheath 24 functionally joined to the vacuum source is axially positioned within the lumen of the elongated member 12. The elongated member 12 may be any one of the elongated members illustrated in FIG. 1A-1C, 2A-2D, or 3A-3D and described in the corresponding text.

The first sheath 4 and the second sheath 24 can be any shape suited to its function. For example, the sheath 4 or sheath 24 can be tubular or funnel shape. The sheath 4 or sheath 24 can have a lumen of uniform or variable diameter. For example, the sheath 4 or sheath 24 in a particular embodiment includes a flared distal end. In another embodiment, the sheath 4 or sheath 24 comprises an invertible sleeve.

Figure 6:
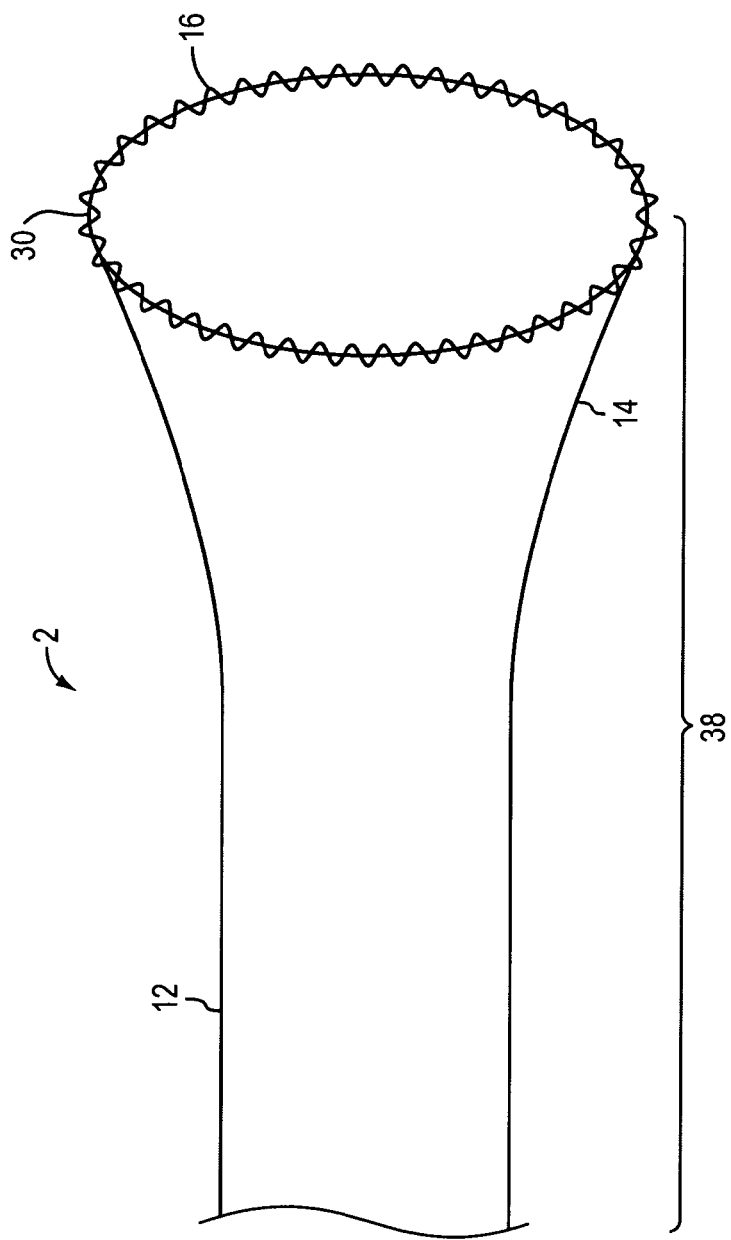
FIG. 6 is a schematic side view of a distal end of a device for treating cardiac tissue, the device comprising an elongated member having a first material and a second material interwoven with a portion of the first material, according to an illustrative embodiment of the invention.

FIG. 6 is a schematic side view of a distal end 38 of a device 2 for treating cardiac tissue, the device 2 comprising an elongated member 12 having a first material 14 and a second material 16 interwoven with a portion of the first material 14, according to an illustrative embodiment of the invention. In one embodiment, the second material 16 of the elongated member 12 is an energy transferring material. The elongated member 12 includes, for example, a flared distal end 30. The portion of the elongated member 12 having at least a portion of the interwoven second material 16 is located on the flared distal end 30. In a further embodiment, the elongated member 12 comprises a uniform fixed diameter. In other embodiments, the elongated member 12 comprises a lumen that is functionally joined to a vacuum source for the application of negative pressure to cardiac tissue.

Another aspect of the invention features a method for treating cardiac tissue. The method comprises the steps of advancing a device 2 according to the invention to a position adjacent to cardiac tissue 18 in need of treatment, the device 2 includes a sheath 4 and at least one elongated member 12 slidably disposed with a lumen 10 of the sheath 4. In one embodiment, the elongated member 12 includes a first material 14 and a second material 16. At least a portion of the second material 16 is interwoven with a portion of the first material 14. As described above with respect to other embodiments, the second material 16 is capable of transferring energy, for example, electromagnetic energy, from an energy source. According to this embodiment, the method comprises the step of advancing the elongated member 12 through the lumen 10 of the sheath. At least a portion of the second material 16 is placed into contact with cardiac tissue in need of treatment 18. The method further includes the step of applying energy from the energy source to the second material 16 to transfer energy to the cardiac tissue 18 in need of treatment.

In one embodiment according to this aspect of the invention, the energy applied to the cardiac tissue includes one of microwave, infrared, visible and ultraviolet light waves, x-ray, gamma ray, or cosmic ray. In another embodiment, the energy is radio frequency energy.

According to a further embodiment of the method of the invention, an operator provides an elongated member 12 including a wire having a hairpin turn 36 at a distal end 33 of the elongated member 12 to form an open ended loop having two ends 52 of the wire at a proximal end of the elongated member 12. At least one end 52 of the wire is operatively joined to an actuator 32. Actuating the actuator 32 in the distal direction unfurls a portion of the elongated member 12 from the lumen 10 of the sheath 4 and moves the distal end 36 of the elongated member 12 in the distal direction. In an additional embodiment, the method further comprises the step of actuating the actuator 32 to move the elongated member 12 distally to place at least a portion of the second material 16 in contact with the cardiac tissue 18 in need of treatment. In a further embodiment, actuating the actuator 32 to move the elongated member 12 in the proximal direction retracts a portion of the elongated member 12 within the lumen 10 of the sheath 4 and moves the distal end 36 of the elongated member 12 in the proximal direction.

A further embodiment of the invention includes an additional step of attaching a vacuum source to the lumen 10 of the sheath 4. According to this embodiment, a vacuum or negative pressure, i.e., suction, is applied to the cardiac tissue 18 to draw the cardiac tissue 18 toward the device 2. In another embodiment, the device 2 comprises a second sheath 24 having a lumen 26, and the method comprises an additional step of attaching a vacuum source to the lumen 26 of the second sheath 24. According to this embodiment, a vacuum can be applied to cardiac tissue to draw the tissue toward the device 2. In both of these embodiments, the cardiac tissue drawn toward the device 2 is contacted with the second material 16 and energy is transferred from the second material 16 to the tissue 18. The vacuum or negative pressure can also be maintained on the tissue while the energy is being applied to the tissue.

A further aspect of the invention includes a method for treating cardiac tissue comprising the step of advancing a device 2 to a position adjacent to cardiac tissue in need of treatment, the device 2 having at least one elongated member 12 comprising a first material 14 and a second material 16. At least a portion of the second material 16 is interwoven with at least a portion of the first material 14. The second material 16 is capable of transferring energy from an energy source to a target tissue, for example, cardiac tissue. The method further comprises the steps of advancing the elongated member 12 through the body of a patient until at least a portion of the second material 16 comes into contact with the cardiac tissue in need of treatment, and applying the energy source to the second material 16 to transfer energy to the cardiac tissue in need of treatment.

In yet another aspect, the invention provides methods for percutaneously closing a PFO using a device 2 such as the device according to the invention depicted in FIGS. 1-6. In one exemplary embodiment, an operator, e.g., a physician, advances the device 2 into the patient's heart with the elongated member 12 retracted within the lumen 10 of the sheath 4. The operator then positions the distal end 6 of the sheath 4 in the right atrium proximate the PFO. With the device 2 positioned as such, the elongated member 12 is deployed into the tunnel of the PFO. As described above, the elongated member 12 is manipulated such that the portion of the elongated member comprising the interwoven second material 16 is exposed to the patient's tissue surface located within the tunnel of the PFO. The second material 16 is connected to an energy source, and energy is transferred from the second material 16 to the tissue surface to close the PFO. The physician then retracts the elongated member 12 from the PFO and removes the device 2 from within the patient.

In a similar embodiment, the device 2 comprising the elongated member 12 is advanced within a patient as described above and is placed adjacent to the right atrial wall of the heart. The elongated member 12 comprises a vacuum which is placed in contact with the right atrial wall, and the portion of the elongated member 12 comprising the interwoven second material 16 is placed in contact with the tissue of the right atrial wall. The vacuum is then activated, attaching the elongated member 12 to the right side of the fossa ovalis. Energy is then delivered to the second material 16 from an energy source, and the energy is transferred from the second material 16 to the fossa ovalis. The energy is absorbed by the surrounding cardiac tissue to close the PFO.

In yet another embodiment of the method according to the invention, the elongated member of the device described herein may be used to delivery energy to the tissues within the tunnel of a PFO as described in co-owned application titled, "In tunnel electrode for sealing intra-cardiac defects", co-filed on the same date as the instant application and incorporated by reference in its entirety herein.

Variations, modifications, and other implementations of what is described herein will occur to those of ordinary skill in the art without departing from the spirit and the scope of the invention. The invention is not to be defined only by the preceding illustrative description.

What is claimed is:

1. An energy transferring medical device, comprising:
   one elongated member comprising a sleeve with an interior surface, wherein a portion of the sleeve is adapted to invert at a distal end of the elongated member and the interior surface of inverted portion of the sleeve forms an exterior surface of the elongated member, wherein the distal end of the elongated member includes a hairpin turn and the sleeve comprises a first substantially non-conductive material and a second energy transferring material at a portion of the sleeve, interwoven with the first substantially non-conductive material along at least a portion of the hairpin turn; and
   an actuator operatively joined to the proximal end of the elongated member, wherein movement of the actuator causes rotational movement of the elongated member about a longitudinal axis of the sleeve.

2. The device of claim 1 wherein the elongated member comprises a first position in which the portion of the elongated member comprising the second energy transferring material is located on the interior surface of the elongated member.

3. The device of claim 2 wherein movement of the actuator in a proximal direction places the elongated member in a second position wherein the portion of the elongated member comprising the second energy transferring material is relocated to the exterior surface of the elongated member.

4. The device of claim 1 wherein the elongated member comprises a first position in which the portion of the elongated member comprising the second energy transferring material is located on the exterior surface of the elongated member.

5. The device of claim 4 wherein movement of the actuator in a proximal direction places the elongated member in a second position wherein the portion of elongated member comprising the second energy transferring material is relocated to the interior surface of the elongated member.

6. The device of claim 1 wherein the second energy transferring material is selected from the group consisting of copper, gold, platinum, silver, iron, lithium, cobalt, nickel, and chromium, or a combination thereof.

7. The device of claim 1 wherein the second energy transferring material comprises a glass or ceramic material.

* * * * *